(12) United States Patent
Griswold

(10) Patent No.: US 8,226,705 B2
(45) Date of Patent: Jul. 24, 2012

(54) METHODS FOR FORMING AN ORTHOGONAL END ON A HELICAL STENT

(75) Inventor: Erik Griswold, Penngrove, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 198 days.

(21) Appl. No.: 12/693,571

(22) Filed: Jan. 26, 2010

(65) Prior Publication Data

US 2011/0071615 A1   Mar. 24, 2011

Related U.S. Application Data

(60) Provisional application No. 61/243,600, filed on Sep. 18, 2009, provisional application No. 61/243,578, filed on Sep. 18, 2009, provisional application No. 61/243,581, filed on Sep. 18, 2009, provisional application No. 61/243,582, filed on Sep. 18, 2009, provisional application No. 61/243,592, filed on Sep. 18, 2009, provisional application No. 61/243,597, filed on Sep. 18, 2009.

(51) Int. Cl.
*A61F 2/82* (2006.01)

(52) U.S. Cl. ...................... 623/1.22; 623/1.15

(58) Field of Classification Search ................. 623/1.15, 623/1.16, 1.22, 23.7
See application file for complete search history.

(56) References Cited

U.S. PATENT DOCUMENTS

| | | |
|---|---|---|
| 2,153,936 A | 4/1939 | Owens et al. |
| 3,185,185 A | 5/1965 | Pfund |
| 4,047,544 A | 9/1977 | Seaborn et al. |
| 4,886,062 A | 12/1989 | Wiktor |
| 5,019,090 A | 5/1991 | Pinchuk |
| 5,092,877 A | 3/1992 | Pinchuk |
| 5,133,732 A | 7/1992 | Wiktor |
| 5,226,913 A | 7/1993 | Pinchuk |
| 5,304,200 A | 4/1994 | Spaulding |
| 5,314,472 A | 5/1994 | Fontaine |
| 5,324,472 A | 6/1994 | Page et al. |
| 5,370,683 A | 12/1994 | Fontaine |
| 5,443,498 A | 8/1995 | Fontaine |
| 5,527,354 A | 6/1996 | Fontaine et al. |
| 5,549,663 A | 8/1996 | Cottone, Jr. |
| 5,653,727 A | 8/1997 | Wiktor |
| 5,716,396 A | 2/1998 | Williams, Jr. |
| 5,895,406 A | 4/1999 | Gray et al. |
| 5,902,266 A | 5/1999 | Leone et al. |

(Continued)

FOREIGN PATENT DOCUMENTS

EP   945107   9/1999

(Continued)

*Primary Examiner* — David H Willse
*Assistant Examiner* — Tiffany Shipmon

(57) ABSTRACT

A method of manufacturing a stent includes forming a wave form having a plurality of struts and a plurality of crowns. Each crown connects two adjacent struts. The wave form has a center and two portions extending from opposite sides of the center. The method includes wrapping a first portion of the wave form about a longitudinal axis in a first direction at a first pitch angle, starting at the center of the wave form, to define at least one turn oriented at the first pitch angle, and wrapping a second portion of the wave form about the longitudinal axis in a second direction that is opposite the first direction at a second pitch angle, starting at the center of the wave form, to define at least one turn oriented at the second pitch angle. The first pitch angle is opposite the second pitch angle.

16 Claims, 3 Drawing Sheets

U.S. PATENT DOCUMENTS

| | | |
|---|---|---|
| 5,913,897 A | 6/1999 | Corso, Jr. et al. |
| 6,042,597 A | 3/2000 | Kveen et al. |
| 6,117,165 A | 9/2000 | Becker |
| 6,136,023 A | 10/2000 | Boyle |
| 6,190,406 B1 | 2/2001 | Duerig et al. |
| 6,203,569 B1 | 3/2001 | Wijay |
| 6,342,067 B1 | 1/2002 | Mathis et al. |
| 6,355,059 B1 | 3/2002 | Richter et al. |
| 6,423,091 B1 | 7/2002 | Hojeibane |
| 6,432,132 B1 | 8/2002 | Cottone et al. |
| 6,447,540 B1 | 9/2002 | Fontaine et al. |
| 6,503,270 B1 | 1/2003 | Richter et al. |
| 6,610,086 B1 | 8/2003 | Kock et al. |
| 6,656,219 B1 | 12/2003 | Wiktor |
| 6,730,117 B1 | 5/2004 | Tseng et al. |
| 6,736,844 B1 | 5/2004 | Glatt et al. |
| 6,878,162 B2 | 4/2005 | Bales et al. |
| 6,923,828 B1 | 8/2005 | Wiktor |
| 6,969,402 B2 | 11/2005 | Bales et al. |
| 7,004,968 B2 | 2/2006 | Lootz et al. |
| 7,108,714 B1 | 9/2006 | Becker |
| 7,169,175 B2 | 1/2007 | Cottone, Jr. et al. |
| 7,329,277 B2 | 2/2008 | Addonizio et al. |
| 2002/0095208 A1 | 7/2002 | Gregorich et al. |
| 2003/0083736 A1 | 5/2003 | Brown et al. |
| 2004/0044401 A1 | 3/2004 | Bales et al. |
| 2004/0143318 A1 | 7/2004 | Tseng et al. |
| 2006/0030934 A1 | 2/2006 | Hogendijk et al. |
| 2006/0079955 A1 | 4/2006 | Brown |
| 2007/0203570 A1 * | 8/2007 | Becker ........................ 623/1.16 |
| 2008/0097580 A1 | 4/2008 | Dave |
| 2008/0097582 A1 | 4/2008 | Shanley et al. |
| 2008/0183273 A1 | 7/2008 | Mesana et al. |
| 2008/0288053 A1 | 11/2008 | Addonizio et al. |
| 2008/0289389 A1 | 11/2008 | Fitch et al. |
| 2008/0294241 A1 | 11/2008 | Addonizio et al. |
| 2008/0306583 A1 | 12/2008 | Bashiri et al. |
| 2008/0319529 A1 | 12/2008 | Krivoruchko et al. |
| 2008/0319534 A1 | 12/2008 | Birdsall et al. |
| 2008/0319535 A1 | 12/2008 | Craven et al. |
| 2009/0005848 A1 | 1/2009 | Strauss et al. |
| 2009/0024207 A1 | 1/2009 | Addonizio et al. |
| 2009/0036976 A1 | 2/2009 | Beach et al. |

FOREIGN PATENT DOCUMENTS

| | | |
|---|---|---|
| EP | 1155664 | 11/2007 |
| FR | 2793673 A1 | 11/2000 |
| GB | 2281865 | 3/1995 |
| WO | WO2007/095466 | 8/2007 |
| WO | WO2008/028964 | 3/2008 |
| WO | WO2008/100783 | 8/2008 |

* cited by examiner

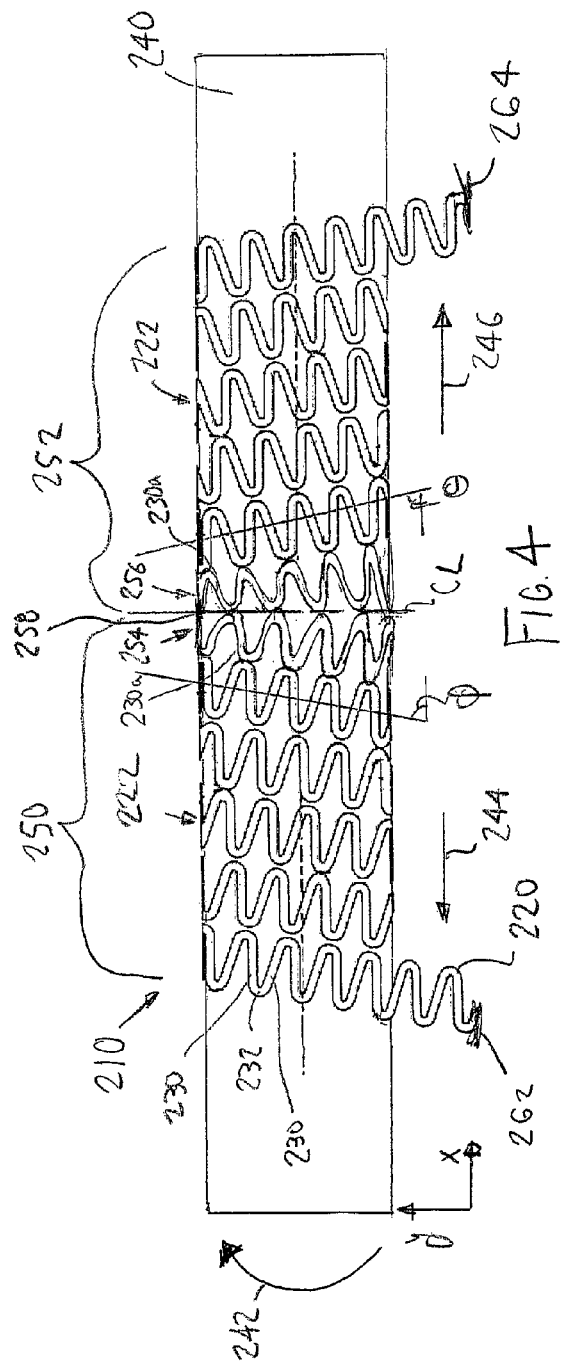
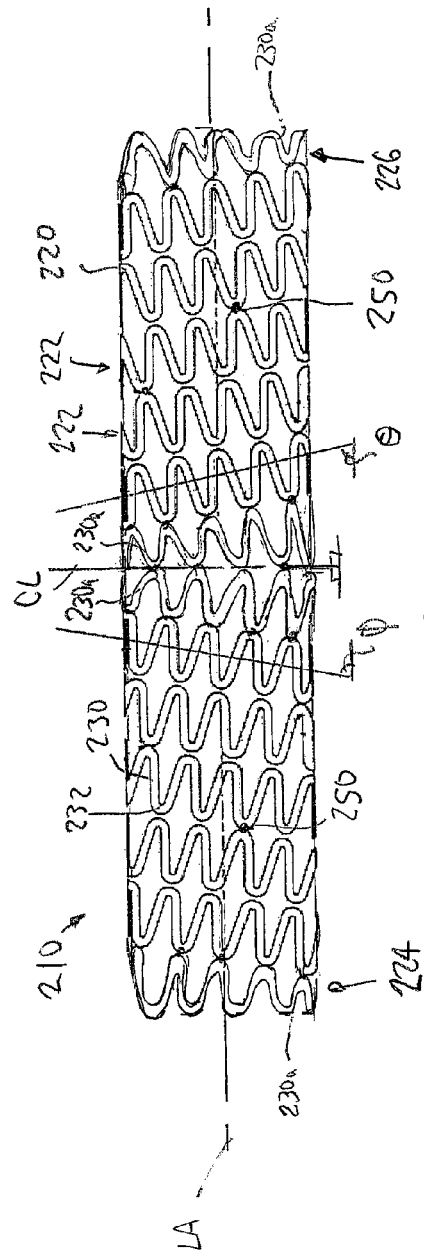

METHODS FOR FORMING AN ORTHOGONAL END ON A HELICAL STENT

CROSS-REFERENCE TO RELATED APPLICATIONS

This application claims the benefit of priority from U.S. Provisional Patent Application Ser. No. 61/243,600, filed on Sep. 18, 2009, the entire content of which is incorporated herein by reference. This application also claims the benefit of priority from U.S. Provisional Patent Application Ser. Nos. 61/243,578, 61/243,581, 61/243,582, 61/243,592, and 61/243,597, all filed on Sep. 18, 2009, the entire contents of all of which are incorporated herein by reference.

BACKGROUND OF THE INVENTION

1. Field of the Invention

The present invention is generally related to a method of manufacturing a helical stent having an orthogonal end relative to a longitudinal axis of the stent, as well as to a helical stent having an end that is orthogonal to the longitudinal axis of the stent.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a delivery system that includes a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s), may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped around the longitudinal axis at a non-perpendicular angle. Helical stents tend to have ends that are not perpendicular to the longitudinal axis due to the pitch of the helix.

Other helical stents have transitions near the ends of the stent to compensate for the helical center portion of the stent, yet provide ends that are orthogonal to the longitudinal axis. Because both ends of the stent are modified from the remaining pattern of the stent, it may be difficult to design a stent that has the same flexibility along the length of the stent, as well as uniform radial expansion properties.

SUMMARY OF THE INVENTION

It is desirable to provide a helical stent that has ends that are orthogonal or perpendicular to the longitudinal axis of the stent, and also has more uniform properties along the length of the stent, both in terms of flexibility and radial expansion.

It is an aspect of the present invention to provide a method of manufacturing a stent. The method includes forming a wave form having a plurality of struts and a plurality of crowns. Each crown connects two adjacent struts. The wave form has a center and two portions extending from opposite sides of the center. The method also includes wrapping a first portion of the wave form about a longitudinal axis in a first direction along the longitudinal axis at a first pitch angle, starting at the center of the wave form, to define at least one turn oriented at the first pitch angle. The method also includes wrapping a second portion of the wave form about the longitudinal axis in a second direction along the longitudinal axis that is opposite the first direction at a second pitch angle, starting at the center of the wave form, to define at least one turn oriented at the second pitch angle. The first pitch angle and the second pitch angle are substantially opposite to each other.

It is an aspect of the present invention to provide a stent that includes a wave form comprising a plurality of struts and a plurality of crowns. Each crown connects two adjacent struts within the wave form, the wave form being wrapped around a longitudinal axis to define a plurality of turns. At least one of the turns defines a first helix oriented at a first pitch angle, and at least one of the turns defines a second helix oriented at a second pitch angle. The first pitch angle and the second pitch angle are oriented substantially opposite to each other.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 4 schematically illustrates a method of manufacturing a helical stent in accordance with an embodiment of the present invention; and FIG. 5 schematically illustrates an embodiment of a helical stent manufactured by the method of FIG. 4.

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
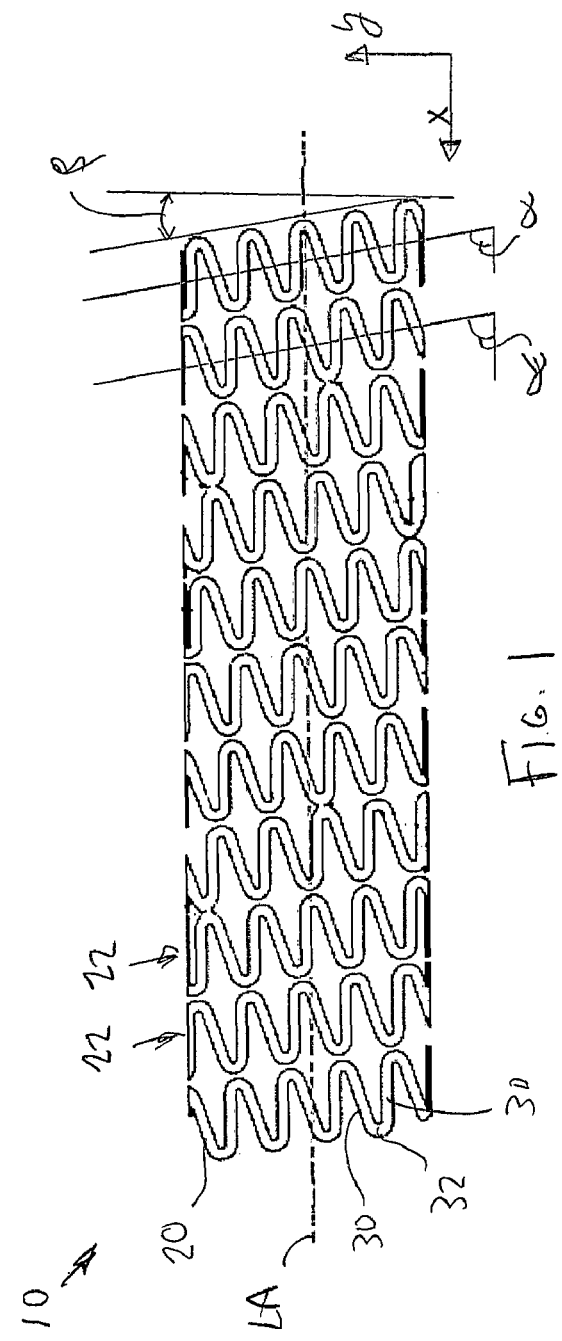
FIG. 1 schematically illustrates an embodiment of a helical stent of the prior art.
Figure 3:
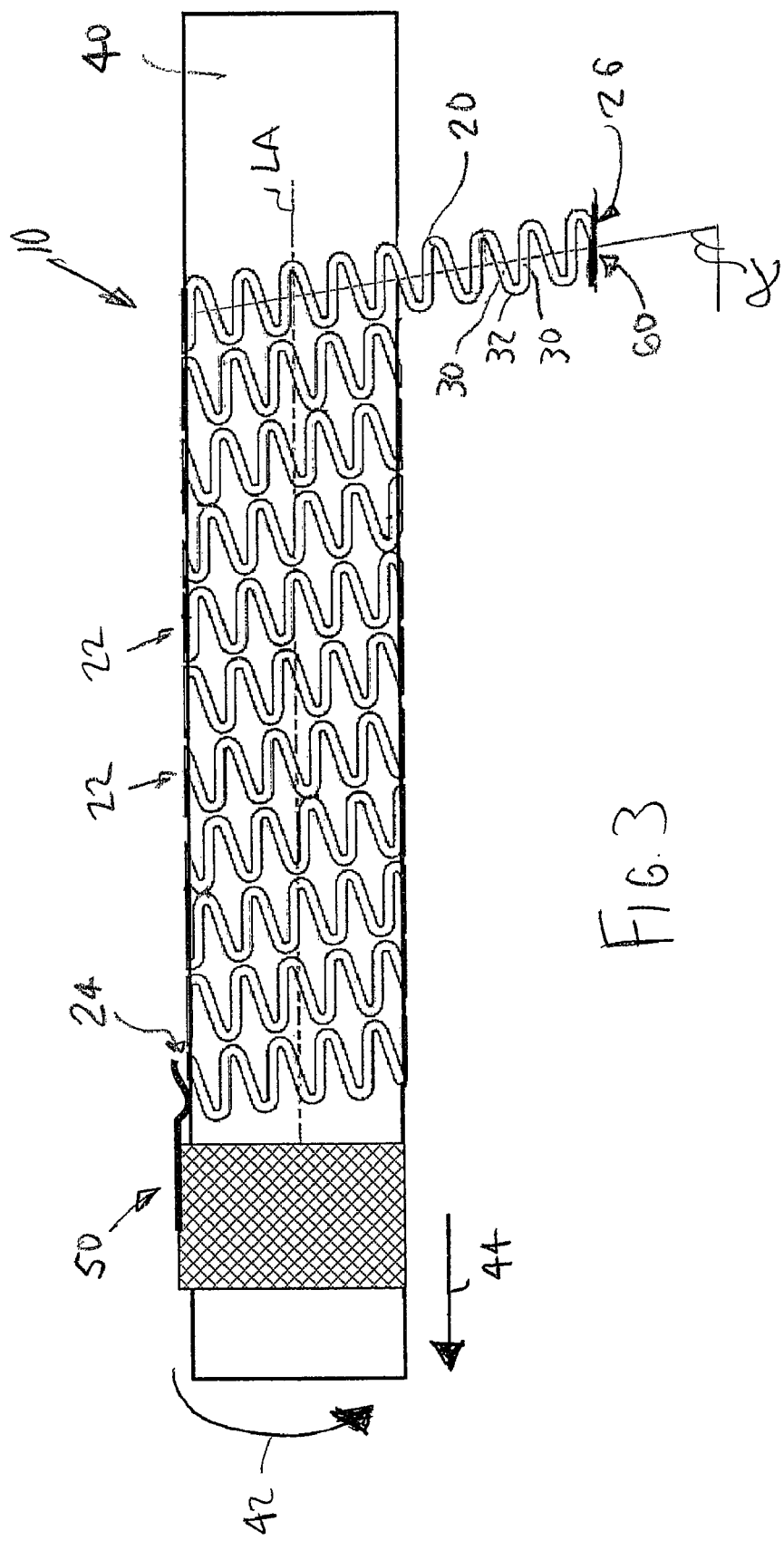
FIG. 3 schematically illustrates a method of manufacturing the helical stent of FIG. 1.

FIG. 1 illustrates an embodiment of a helical stent 10 known in the prior art. The stent 10 is generally cylindrical in shape and has a longitudinal axis LA extending through the center of the stent 10. The stent 10 includes a continuous wave form 20 that includes a plurality of turns 22 that are created when the wave form 20 is wrapped around the longitudinal axis LA during manufacturing of the stent 10. A mandrel 40 or rod that is aligned with the longitudinal axis LA may be used to support the wave form 20 as the wave form 20 is wrapped around the longitudinal axis LA, as shown in FIG. 3 and described in further detail below.

As illustrated in FIG. 1, the wave form 20 includes a plurality of struts 30 and a plurality of crowns 32. Each crown 32 is a curved portion or turn within the wave form 20 that connects adjacent struts 30 to define the continuous wave form 20. The struts 30 are substantially straight portions of the wave form 20 and have substantially the same length. In other embodiments, the struts 30 may be slightly bent or have other shapes, such as a sinusoidal wave, for example.

As illustrated in FIG. 1, the wave form 20 is wrapped around the longitudinal axis LA at a constant pitch so that the wave form 20 generally defines a helical coil a constant helical angle, or pitch angle α. The ends of the stent 10 are not orthogonal to the longitudinal axis LA and are angled relative to what would be orthogonal to define an angle β, which is equal to 90° minus α. It is desirable for the ends of the stent to be orthogonal to the longitudinal axis, i.e. for β to equal zero.

Figure 2:
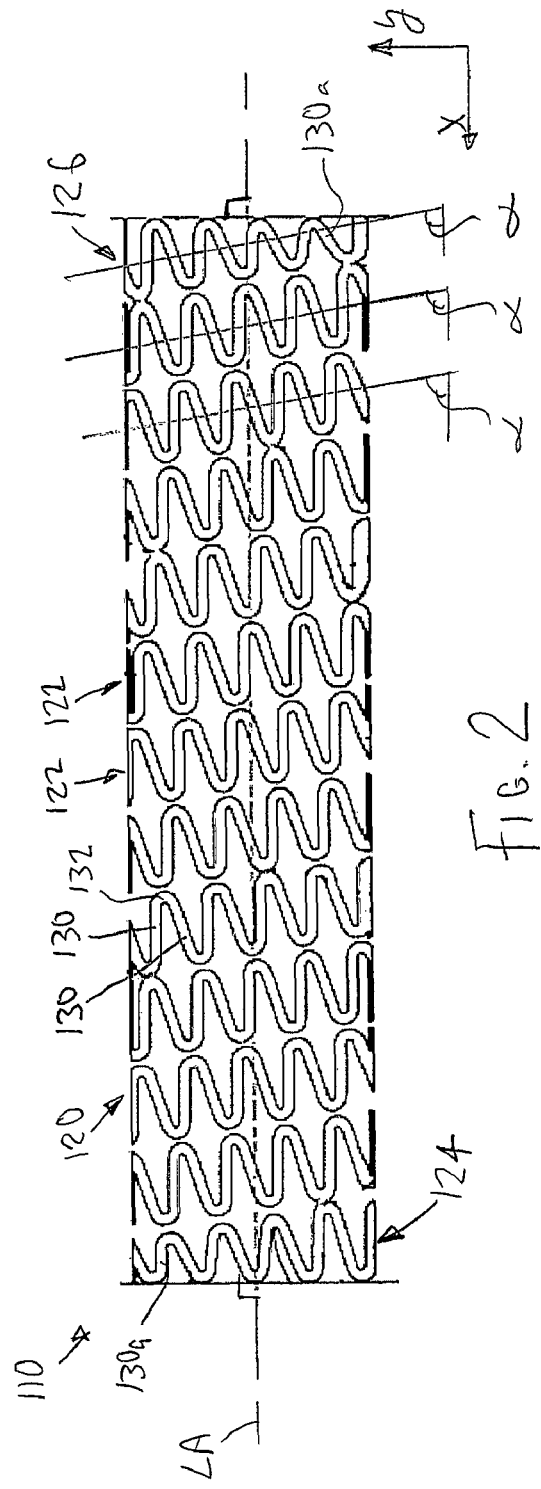
FIG. 2 schematically illustrates an embodiment of a helical stent of the prior art.

FIG. 2 illustrates an embodiment of a stent 110 known in the prior art. Like the stent 10 illustrated in FIG. 1, the stent 110 is generally a helical stent that includes a continuous wave form 120 that includes a plurality of turns 122 that are created when the wave form 120 is wrapped around the longitudinal axis LA during manufacturing of the stent 110.

As illustrated in FIG. 2, the wave form 120 includes a plurality of struts 130 and a plurality of crowns 132. Each crown 132 is a curved portion or turn within the wave form 120 that connects adjacent struts 130 to define the continuous wave form 120. As shown in FIG. 2, the struts 130 are substantially straight portions of the wave form 120.

As illustrated in FIG. 2, the wave form 120 is wrapped around the longitudinal axis LA at a constant pitch so that the wave form 120 generally defines a helical coil a constant helical angle, or pitch angle α. In the illustrated embodiment, the struts 130 of all but end turns 124, 126 have substantially the same length. The end turns 124, 126 each include struts of different lengths, including struts 130a that are shorter than the length of the struts 130 of the turns 122. The shorter struts 130a of the end turns 124, 126 are designed to allow the ends of the stent 110 to be orthogonal to the longitudinal axis LA, when the end turns 124, 126 are wrapped at the pitch angle α.

The end turns 124, 126 of the stent 110 are not mirror images of each other, i.e., the shorter struts 130a are located on opposite sides of the longitudinal axis LA, which may create non-uniform tracking and expansion behavior along the length of the stent 110.

FIG. 3 illustrates a method of manufacturing the stent 10 of FIG. 1. The stent of FIG. 2 may also be manufactured using the same method, as understood by one of ordinary skill in the art. As illustrated in FIG. 3, one end 24 of the wave form 20 is pressed against the mandrel 40 with a pressing member 50 that is attached to the mandrel 40 so that it rotates and translates with the mandrel 40. The other end 26 of the wave form 20 may be held with a suitable structure 60 that is configured to hold the other end 26 of the wave form 20 as the wave form 20 is wrapped around the mandrel 40 so that the helical angle α stays substantially constant.

The mandrel 40 may be rotated and translated, as indicated by arrows 42 and 44, respectively, at a suitable speed so that the wave form 20 wraps around the mandrel 40, and the longitudinal axis LA, to create the turns 22. The number of revolutions of the mandrel 40 determines the number of turns 22 in the stent 10. As discussed above, the wave form may be varied so that the end turns of the stent are substantially orthogonal or perpendicular to the longitudinal axis, such as the end turns 124, 126 of the stent 110 illustrated in FIG. 2.

FIG. 4 illustrates a method of manufacturing a stent 210 according to an embodiment of the present invention. An embodiment of the stent 210 manufactured by the method illustrated in FIG. 4 is shown in FIG. 5. As illustrated, the stent 210 is generally cylindrical in shape and has a longitudinal axis LA extending through the center of the stent 210. The stent 210 includes a continuous wave form 220 that includes a plurality of turns 222 that are created when the wave form 220 is wrapped around the longitudinal axis LA during manufacturing of the stent 210. A mandrel 240 or rod that is aligned with the longitudinal axis LA may be used to support the wave form 220 as the wave form 220 is wrapped around the longitudinal axis LA, as shown in FIG. 4.

The wave form 220 includes a plurality of struts 230 and a plurality of crowns 232. Each crown 232 is a curved portion or turn within the wave form 220 that connects adjacent struts 230 to define the continuous wave form 220. As shown in FIGS. 4 and 5, the struts 230 are substantially straight portions of the wave form 220. In other embodiments, the struts 230 may be slightly bent or have other shapes, such as a sinusoidal wave, for example.

As illustrated in FIG. 4, a first portion 250, which may be about one-half, of the wave form 220 is wrapped around the longitudinal axis LA at a constant helical or pitch angle φ so that the portion 250 of the wave form 220 generally defines a helical coil at the constant pitch angle φ, relative to the longitudinal axis. A second portion 252, which may be about one-half, of the wave form 220 is wrapped around the longitudinal axis LA at a constant helical or pitch angle θ so that the second portion 252 of the wave form 220 generally defines a helical coil at the constant pitch angle θ, relative to the longitudinal axis. In the illustrated embodiment, the pitch angles φ and θ have substantially the same magnitude, but are positive and negative, respectively, in the x-y coordinate system depicted in FIG. 4, and may therefore be considered to be substantially opposite to each other with respect to a centerline CL of the stent 210. The first and second portions 250, 252 of the wave form 220 are on opposite side of the centerline CL of the stent 210, as illustrated in FIG. 4, and are connected to each other via the material that is used to form the wave form 220.

The part of the wave form 220 that is used to create the first turns 254, 256 of the first and second portions 250, 252, which may be the center part of the wave form 220, may include struts 230a that are shorter than the struts 230 used in the other turns 222 of the stent 210. This may allow the crowns 232 of the first turn 254 of the first portion 250 that face the centerline CL to substantially align with the centerline CL. This may also allow the crowns 232 of the first turn 256 of the second portion 252 that face the centerline CL to substantially align with the centerline CL so that when the wave form 220 is wrapped around the longitudinal axis LA at the pitch angles φ and θ, there is only a small gap between the crowns 232 that face each other at the centerline CL. In other words, the wave form 220 may be configured so that the first turns 254, 256 of each portion 250, 252 of the stent 210 provide transitions from the orthogonal centerline CL to the respective pitch angles φ and θ.

To form the stent 210, a center 258 of the wave form 220 is fixed to the mandrel 240 by any suitable means, such as a clamp. Opposing ends of the wave form 220 may be held and guided by suitable structures 262, 264 that are configured to translate the first and second portions 250, 252 of the wave form 220 in opposing directions, represented by arrows 244, 246, respectively, as the mandrel is rotated, as represented by arrow 242. In contrast to the manufacturing of the stent 10 that is illustrated by FIG. 3, in which the stent 10 created from one end to the other, the stent 210 is created from the center outward.

As illustrated in FIG. 5, the wave form 220 may also be configured to provide end turns 224, 226 that provide ends of the stent 210 that are substantially orthogonal to the longitudinal axis LA. This may be done by having shorter struts 230a in the corresponding portion of the wave form 220 so that when the mandrel 240 is rotated one last time to create the end turns 224, 226, the ends of the stent are substantially perpendicular to the longitudinal axis LA. In an embodiment, the wave form 220 may include a plurality of transitional turns near the ends of the stent that are configured to gradually transition the pitch angles of the turns of the first and second portions 250, 252, i.e., the pitch angles φ and θ, to the end turns 224, 226 that allow for the ends of the stent to be substantially perpendicular to the longitudinal axis LA. For example, instead of having one turn at each end of the stent that provides the entire transition from the pitch angles φ and θ to the substantially orthogonal ends of the stent, a plurality of turns like the end turns 224, 226 may be used. In such an embodiment, the lengths of the struts in such turns may be more gradually shortened in each of the transitioning turns.

In an embodiment, the pitch angles φ and θ may not be constant for the first and second portions 250, 252, but instead may be gradually increased in magnitude so that by the last turn 222 of the mandrel 250 to form the end turns 224, 226, the pitch angles φ and θ have increased to about 90°. In an embodiment, the end turns 224, 226 of the stent 210 may be separate pieces that may be connected to the wave form 220 after the turns 222 of the stent 210 have been created with the rotation of the mandrel 250. The illustrated embodiments described herein should not be considered to be limiting in any way.

As illustrated in FIG. 5, the stent 210 may include a plurality of connections 250 that connect selected crowns 232 of adjacent turns 222. The connections 250 may be created by fusing the selected crowns 232 together. As used herein, "fusing" is defined as heating the target portions of materials to be fused together, without adding any additional material, to a level where the material in the target portions flow together, intermix with one another, and form a fusion when the materials cool down to, for example, room temperature. A suitable laser may be used to create the fusion.

In an embodiment, the connections 250 may be created by welding or soldering the selected crowns 232 together. As used herein, "welding" and "soldering" are defined as heating an additional material that is separate from the selected crowns and applying the heated additional material to the selected crowns 232 so that when the additional material cools, the selected crowns 232 are welded or soldered together.

In an embodiment, the connections 250 may be created by fusing, welding, or soldering an additional piece of material (not shown) that extends between selected crowns 232. The additional piece of material may resemble a strut or a portion of a strut, and may be sized to provide spacing between the selected crowns of two adjacent turns, if desired. The illustrated embodiments are not intended to be limiting in any way.

The size of the connections 250 may also be varied according to the desired flexibility and rate of expansion for a given area of the stent 210. In general, the larger the connection 250, i.e. the larger the fusion or weld, the greater the stiffness, and the slower the rate of expansion of the stent in the area of the larger connections.

The embodiments of the stents discussed above may be formed from a wire or a strip of suitable material. In certain embodiments, the stents may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different metals, alloys, or other materials. Embodiments of the stent may also be formed from hollow tubes, or tubes that have been filled with other materials. The aforementioned materials and laminations are intended to be examples and are not intended to be limiting in any way.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A generally cylindrical stent comprising:
a wave form formed from a single continuous wire and comprising a plurality of struts and a plurality of crowns with each crown being formed between two adjacent struts within the wave form, the wave form being wrapped around a longitudinal axis of the stent to define a plurality of turns with each turn being a circumferential wrapping of the wave form around the longitudinal axis, at least one of the turns defining a first helix oriented at a first pitch angle relative to the longitudinal axis, and at least one of the turns defining a second helix oriented at a second pitch angle relative to the longitudinal axis, the first pitch angle and the second pitch angle being of equal magnitude and oriented in substantially opposite directions to each other with respect to a centerline that is orthogonal to the longitudinal axis of the stent.

2. The stent of claim 1, wherein the wave form defines a plurality of turns oriented at the first pitch angle, and a plurality of turns oriented at the second pitch angle.

3. The stent of claim 1, wherein at least some of the crowns are disposed along the centerline of the stent.

4. The stent of claim 1, wherein the stent has ends that are substantially perpendicular to the longitudinal axis.

5. The stent of claim 1, further comprising a plurality of connections that connect selected crowns of adjacent turns.

6. The stent of claim 5, wherein the connections are fusions of the selected crowns of adjacent turns.

7. The stent of claim 5, wherein the connections comprise welds.

8. A generally cylindrical stent comprising:
a wave form formed from a single continuous wire and having a plurality of struts and a plurality of crowns with each crown being formed between two adjacent struts, the wave form defining a first portion that longitudinally extends in a first direction from a centerline that is orthogonal to a longitudinal axis of the stent and a second portion that longitudinally extends in an opposing second direction from the centerline of the stent, wherein the first portion of the wave form defines a plurality of turns with each turn being a circumferential wrapping of the wave form around the longitudinal axis of the stent and with at least one turn being oriented at a first pitch angle relative to the longitudinal axis, the second portion of the wave form defines a plurality of turns with each turn being a circumferential wrapping of the wave form around the longitudinal axis of the stent and with at least one turn being oriented at a second pitch angle relative to the longitudinal axis, and the first pitch angle and the second pitch angle being of equal magnitude and oriented in substantially opposite directions to each other with respect to the centerline of the stent.

9. The stent of claim 8, wherein the plurality of crowns of the first portion and the plurality of crowns of the second portions are disposed aligned along the centerline of the stent.

10. The stent of claim 9, wherein selected crowns of the first portion are disposed adjacent to and opposing crowns of the second portion disposed aligned along the centerline of the stent.

11. The stent of claim 10, wherein selected opposing crowns of the first and second portions disposed aligned along the centerline of the stent are connected to each other by a weld, a fusion or a solder.

12. The stent of claim 8, wherein a final turn of the wave form in each of the first and second portions is oriented substantially perpendicular to the longitudinal axis such that each end of the stent is substantially perpendicular to the longitudinal axis.

13. The stent of claim 12, wherein the plurality of turns of the wave form in the first portion includes at least one transitional turn near the end of the stent that is oriented at a pitch angle having a magnitude between the magnitude of the first pitch angle and 90°.

14. The stent of claim 13, wherein the plurality of turns of the wave form in the second portion includes at least one transitional turn near the end of the stent that is oriented at a pitch angle having a magnitude between the magnitude of the second pitch angle and 90°.

15. The stent of claim 8, wherein selected adjacent crowns within the first and second portions are connected to each other by welds, fusion or solder.

16. The stent of claim 8, wherein a plurality of adjacent turns in the first portion are oriented at the first pitch angle so as to define a helical coil having the first pitch angle and a plurality of adjacent turns in the second portion are oriented at the second pitch angle so as to define a helical coil having the second pitch angle.

\* \* \* \* \*